United States Patent [19]

Trygstad

[11] Patent Number: 5,760,399
[45] Date of Patent: Jun. 2, 1998

[54] MEASUREMENT OF TRANSMISSION SPECTRA OF PHARMACEUTICAL TABLETS

[75] Inventor: W. Marcus Trygstad, Ellicott City, Md.

[73] Assignee: Foss NIRSystems, Inc., Silver Spring, Md.

[21] Appl. No.: 538,293

[22] Filed: Oct. 2, 1995

[51] Int. Cl.[6] ................................................ G01N 21/35
[52] U.S. Cl. .......................... 250/339.07; 250/339.12; 250/341.1; 250/341.2
[58] Field of Search .......................... 250/339.07, 339.12, 250/341.2, 341.1

[56] References Cited

U.S. PATENT DOCUMENTS

| | | | |
|---|---|---|---|
| 4,349,531 | 9/1982 | Mlodozeniec et al. | 424/27 |
| 4,387,990 | 6/1983 | Yazawa et al. | 356/244 |
| 4,415,811 | 11/1983 | Beck et al. | 250/560 |
| 4,882,493 | 11/1989 | Lodder et al. | 250/353 |
| 5,070,874 | 12/1991 | Barnes et al. | 250/339.12 |
| 5,171,995 | 12/1992 | Gast et al. | 250/339.08 |
| 5,214,277 | 5/1993 | Drennen, III | 250/216 |
| 5,235,409 | 8/1993 | Burgi et al. | 356/436 |
| 5,319,200 | 6/1994 | Rosenthal et al. | 250/341.1 |
| 5,338,935 | 8/1994 | Truett et al. | 250/339.06 |
| 5,463,223 | 10/1995 | Wong et al. | 250/339.12 |
| 5,504,332 | 4/1996 | Richmond et al. | 250/341.8 |

*Primary Examiner*—Constantine Hannaher
*Attorney, Agent, or Firm*—Lane, Aitken & McCann

[57] ABSTRACT

In an instrument for making an NIR spectrographic transmission measurement of a pharmaceutical tablet, masking structure is provided to prevent or reduce leakage of radiation around the edge of the tablet. The masking structure (30, 44) constricts the boundary of the light beam so that it is within the boundary of the top surface of the tablet where it impinges upon the top surface. The tablet is received in a well slightly larger than the tablet formed in a tablet locator (20). An aperture (39) is formed in the bottom of the well.

10 Claims, 4 Drawing Sheets

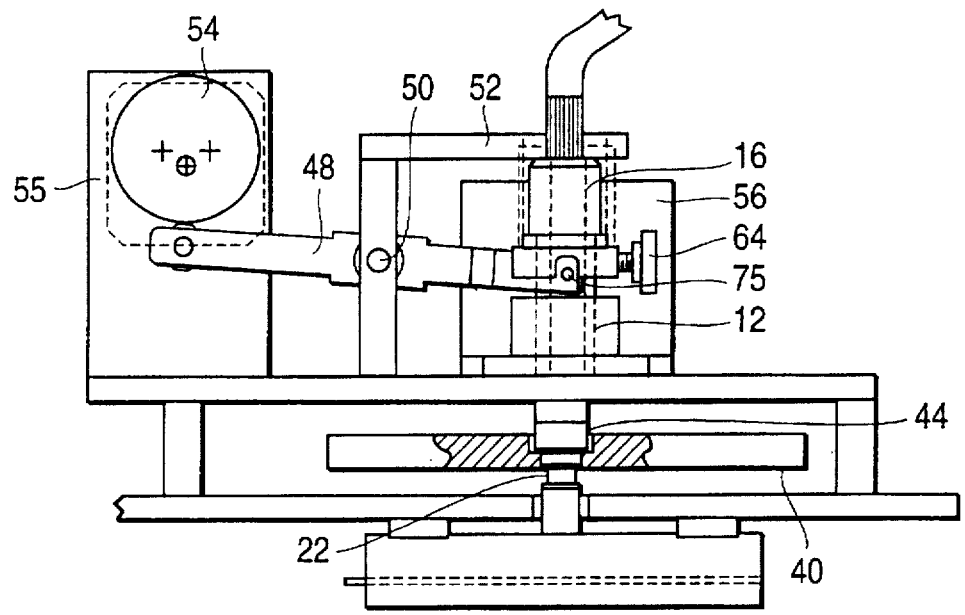
FIG. 3
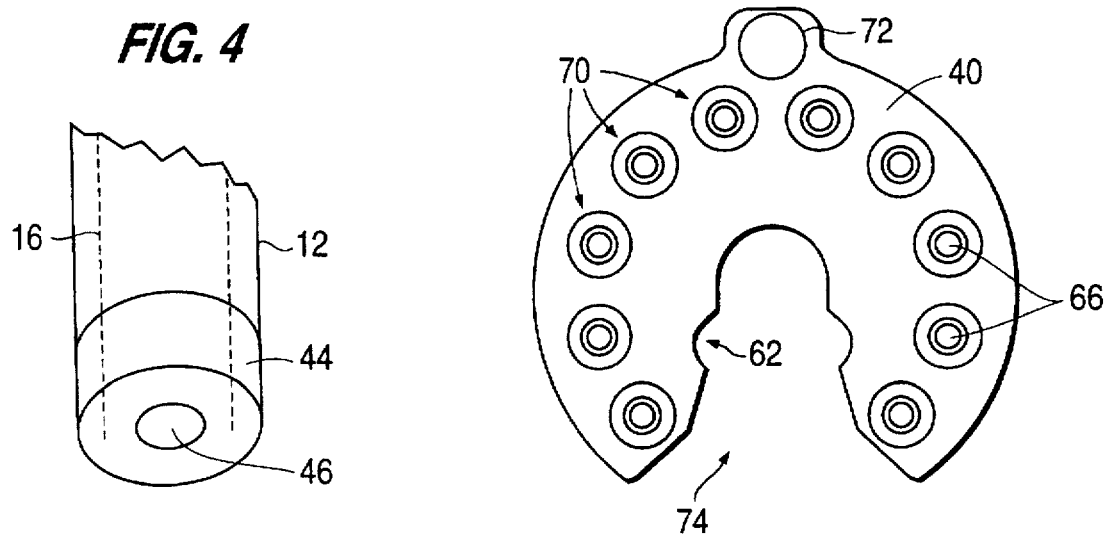
FIG. 4
FIG. 5

MEASUREMENT OF TRANSMISSION SPECTRA OF PHARMACEUTICAL TABLETS

FIELD OF INVENTION

The present invention relates to an apparatus used for spectrometric transmission measurements and, in particular, NIR transmission measurements of tablets containing pharmaceutical compounds.

BACKGROUND OF THE INVENTION

Infrared spectroscopy and more particularly near-infrared ("NIR") spectroscopy is a valuable non-invasive manner to perform both qualitative and quantitative analysis of samples. The equipment required to obtain spectroscopic measurements includes a source of NIR light known as a spectrometer, and a detector. From incident light, either reflected from or transmitted through a sample, information about the sample's constituent make-up can be measured. One important application for spectrometric analysis is the measurements of pharmaceuticals compounds. Because compounds in pharmaceutical doses have different absorbance properties, qualitative and quantitative properties about a sample can be determined by analyzing light either reflected from or transmitted through the sample.

The measurement of solids using NIR spectroscopy techniques is predominately performed using reflectance techniques. Reflectivity measurements involve penetrating only a few microns of the sample's surface one or more times with the light beam. Reflectivity measurements of solids, however, present some disadvantages and significant efforts have been directed at improving their accuracy. Such efforts have included designs which optically enhance the incident NIR energy upon the sample. Notwithstanding the advances, there remain a number of attendant problems and disadvantages with reflectivity measurements. In some cases the active compound of interest may not be present on the surface of a sample but is buried within the matrix and accordingly the active compound of the sample will not be measured using reflective techniques. Furthermore, active compounds may not be evenly distributed throughout the matrix. A sample that is not homogenous may lead to measurements which are not representative. The chemistry of an active compound present on or near the surface of a sample may be affected by coatings on the tablet or exposure to the environment. These factors could also contribute to inaccurate measurement using reflective techniques. Some techniques employing reflectivity measurements require grinding the sample into a powder which effectively excludes this technique as a method of quality control, such as to check for product tampering.

Conventional measuring practices in connection with pharmaceutical tablets have essentially ignored or overlooked the use of transmission measurements. The use of transmission measurements may have been neglected because tablets are opaque and it may have been assumed that NIR light would not be appreciably transmitted through samples. However in many cases, solids which appear opaque will still transmit significant light in the infrared spectrum and transmission measurements can yield useful information.

A further problem which may have contributed to the neglect of transmission measurements in connection with pharmaceutical compounds is the absence of suitable hardware to present the sample between the NIR light source and detector. Pharmaceutical tablets come in a wide variety of sizes and shapes and the hardware employed must be able to easily accommodate the sample to be measured. Accordingly there is a need for a manner in which to conveniently and effectively present small solid samples such as tablets containing pharmaceutical compounds to a spectrometric instrument. Such a manner must ensure that stray radiation does not interfere with the measurement. Any incident light that travels around the sample or leaks can compromise the accuracy of the measurement by causing nonlinear errors in the measurements of absorbance.

The present invention is directed at a transmission measuring device and more particularly a sample positioning device and masking element used in a transmission measuring device. The positioning device and masking element minimizes or eliminates the incidence of stray radiation reaching the detector.

SUMMARY OF THE INVENTION

The present invention is directed at a positioning device or locator designed to convey a solid sample such as a pharmaceutical tablet to a location where a spectrometric measurement will take place. The positioning device, in combination with a masking device prevents light from leaking around the edges of the tablet and adversely interfering with the detection of radiation transmitted through the sample. The reduction or elimination of stray light which has not passed through the sample reaching the detector enables an accurate measurement to be made. The present invention further provides various automated approaches which allows a user to quickly perform multiple spectrometric measurements while incorporating the advantages of the locator and masking element combination.

BRIEF DESCRIPTION OF THE DRAWINGS

FIG. 3 is a side sectional view of a second embodiment of the invention.

FIG. 4 is a fragmented perspective view of the probe and masking hood element.

FIG. 5 is a top view of the sample locator used with the second embodiment of the invention.

DETAILED DESCRIPTION

Figure 1:
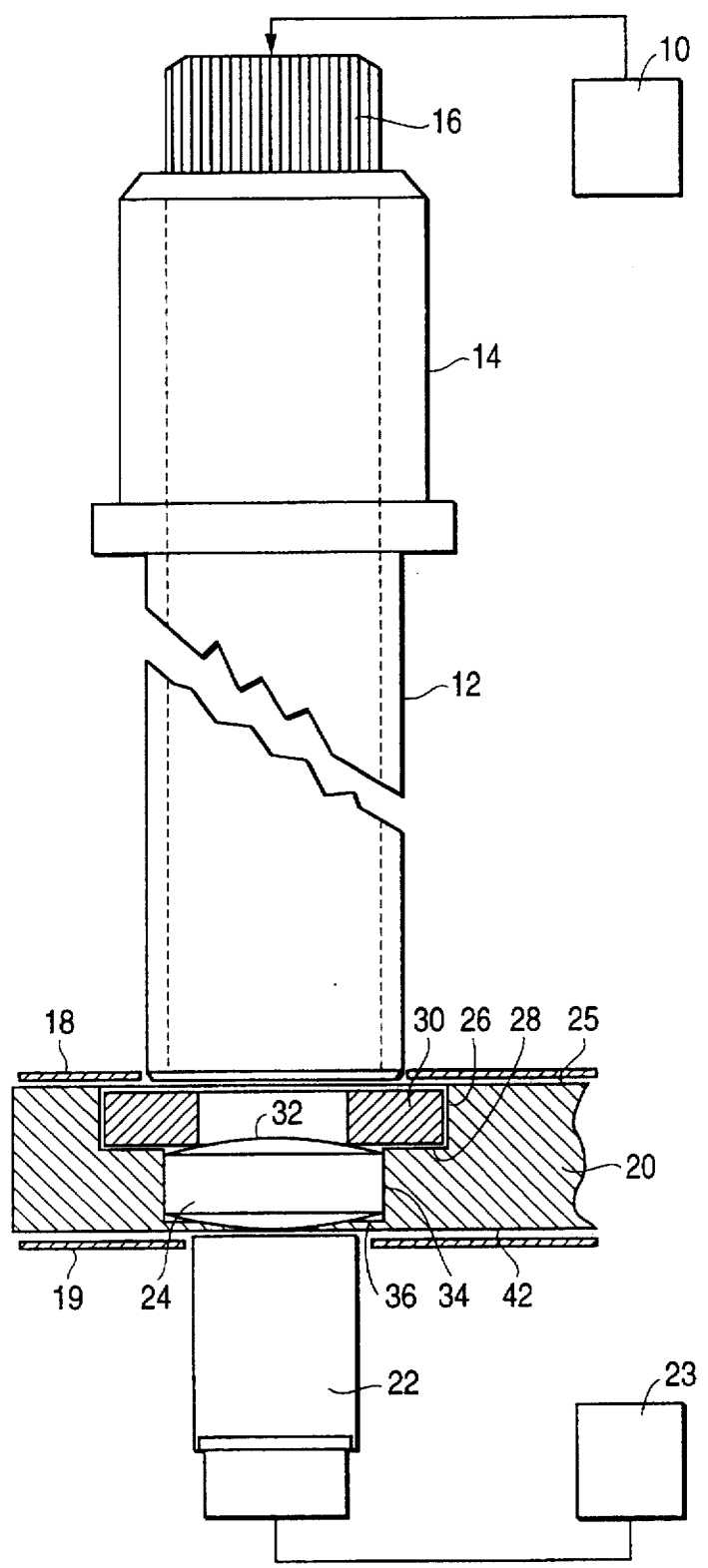
FIG. 1 is a side view in partial cross section of a first embodiment of the invention.

Referring now to FIG. 1, the apparatus according to a first embodiment of the invention has a probe 12 with an outer housing 14 and an inner optic fiber bundle 16. A light source 10 consisting of a grating spectrometer provides narrow bandwidth NIR light to fiber optic bundle 16. In the first embodiment, the probe 12 is mounted in a fixed position above a slot defined by top surface 18 and bottom surface 19 which receives sample locator 20. Positioned directly below the slot and in axial alignment with the probe 12 is detector 22 which detects the amplitude of NIR radiation transmitted through a sample tablet 24. The instrument of the invention is designed to measure pharmaceutical products, but the tablet can comprise any solid integral material which requires measurement. The detector 22 transmits a signal to a computer where the signal 23 is converted to a digital form for analysis of the transmission measurement.

Provided in the top surface 25 of the sample tablet locator 20 is a cylindrical first well defined by sidewall 26 and annular surface 28. Received in the first well is an annular masking element 30 having a center aperture. Masking element 30 has a height less than that of sidewall 26 and an aperture diameter approximately ⅔ or 67% of the diameter of the sample tablet 24. The masking element is sized so that it does not extend above the top surface 25 of the sample locator 20. The bottom surface of the masking element directly engages the top surface 32 of sample tablet 24 at the rim of the center aperture thereof. Concentric with the first well is a second cylindrical well or sample well defined by sidewall 34 and bottom surface 36. The second well receives sample tablet 24.

Figure 2:
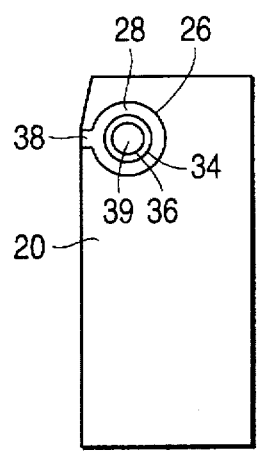
FIG. 2 is a top view of the sample locator according to the first embodiment of the invention.

As best seen in FIG. 2, a top view of the sample locator 20, a slot 38 which is defined by a bottom surface, in the same plane as surface 28, and the vertical sidewalls which intersect with the sidewalls 26 of the first well. The slot 38 thereby connects the first well to the side of the sample tablet locator 20. The slot facilitates the removal of the masking element 30. Also shown in FIG. 2 is aperture 39 which provides a passage from bottom surface 36 to the lower surface 42 of the locator 20.

In use, a sample tablet is first inserted into the second well of the locator. Next, the masking element is placed within the first well and engages the top surface of the tablet. The locator is then manually inserted into the slot defined by surfaces 18 and 19 and aligned between the probe and detector. When the sample is in place, the light source and detector are activated and a measurement is obtained.

The dimensions of the sample tablet locator 20 are precisely formed in relation to the sample tablet to minimize the possibility of light leakage around the sample tablet. It is contemplated that a unique sample locator and masking element will be provided which is custom fit to the particular dimensions of each tablet form which requires analysis. The outer first well of the sample locator 20 has a diameter of 0.600 inches. The second cylindrical well which receives the sample tablet has a diameter 0.004 inches larger than the diameter of the sample tablet. By precisely sizing the diameter of the sample well, the potential for incident light to leak around the sample is significantly minimized. The height of the sidewall of the second well is variable and is designed to be approximately 80% of the height of the sample tablet. By requiring the sidewall height of the second well to be significantly less than the height of the sample tablet, the masking element is ensured to achieve good contact with the top surface of the sample tablet. The sample well should have a minimum sidewall height of approximately 25% of the height of the sample tablet to prevent the tablet from rocking within the well. Through the planar bottom of the second well is an aperture formed with a diameter approximately 67% or two thirds of the diameter of the sample tablet. This aperture is the same size as and is axially aligned with the aperture on the masking element. Both the height and the aperture of the masking element are variable and are sized in accordance with the size of the sample tablet. The distance between the bottom surface of the sample and the detector is approximately 0.005 inches.

FIG. 3 depicts a second embodiment of the invention with a sample tablet in the second well of a tablet locator 40. In this embodiment the probe 12 is mounted in a manner to provide for rectilinear axial movement with respect to the sample and detector. As best seen in FIG. 4 the second embodiment employs a masking hood element 44 which is attached to the movable probe 12. The hood element has a central aperture 46 which is sized at approximately 67% or two thirds the diameter of the sample tablet. Like the first embodiment, the probe's fiber optic bundle 16 is connected to a grating spectrometer which serves as the NIR light source. Masking hood element 44 is generally annular shaped and has a flat bottom surface which directly engages the sample at the rim of the aperture 46. This engagement is similar to the manner of engagement of mask 30 shown in FIG. 1. The masking hood keeps the boundary of the NIR light beam which exits the fiber optic bundle and impinges on the upper surface of the sample to an area less than the area of the top surface of the sample. Keeping the irradiated area smaller than the tablet surface minimizes the leakage of light because it avoids flooding the edges of the sample and the sides of the well containing the sample. This feature minimizes the possibility that NIR radiation will leak around the sample. The diameter of the aperture 46 is the same as the diameter of the exit passage located through the bottom surface of the sample locator.

Attached to the outer housing of probe 14 is rocker arm 48 which effects the movement of the probe. Screw 75 is provided to retain the probe 12 on the rocker arm. Rocker arm 48 pivots at point 50 on a stabilizer arm 52. On the opposite end of the probe, the rocker arm 48 engages a cam 54. Rotation of cam 54 will cause rocker arm 48 to lower and raise the probe to the sample. Rotation of the cam is performed by a motor 55 controlled by a computer. In response to a command, the motor will actuate thereby rotating the cam and causing the rocker arm to lower the probe to the sample. The probe is prevented from further downward movement by direct engagement of the sample and thus the probe rests on the sample when the measurement is taken. As seen in FIG. 3, when the probe is lowered and engages the sample tablet, the masking hood element extends well below the upper planar surface of the sample locator 40.

As shown in FIG. 5, the locator 40 used in this embodiment has ten stepped sample wells generally designated by the reference numeral 70 arranged in an arcuate configuration. Tab 72 is provided for handling the locator and opening 74 provides for sliding the locator onto a hub. The wells 75 in locator 40 are essentially the same as those described in connection with the first embodiment however they do not require a slot feature like slot 38.

Figure 6:
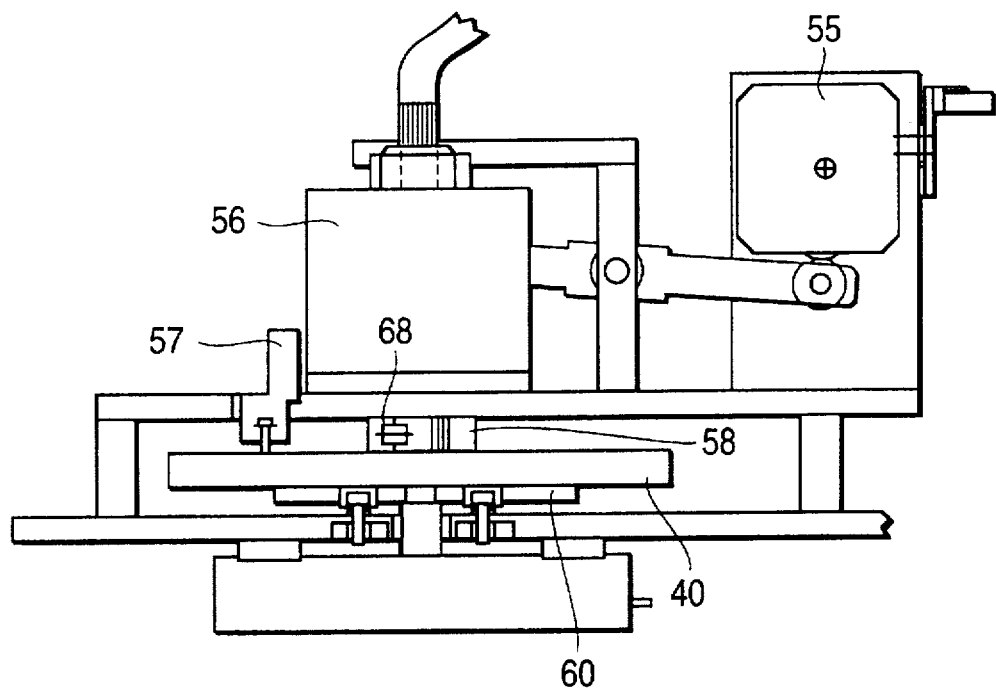
FIG. 6 is a side sectional view of the second embodiment of the invention showing the hub and turntable.

A computer also controls activation of stepper motor 56 shown in FIG. 6, which turns both hub 58 and turntable 60 on which the locator 40 rests. The diameter of the turntable is less than the diameter of the locator so the bottom apertures 66 through the locator remain open and unimpeded. The locator is retained on the hub by a spring clip 68 which engages a recess 62 provided on locator 40. The motor 56, hub 58 and turntable 60 provides for the sequential presentation of samples to the probe. The motor 56 is synchronized with motor 55 so that the probe is raised and lowered on to the samples when a sample well on the locator is aligned under the probe. A sensor 57 is provided to detect the position of the locator.

Figure 7:
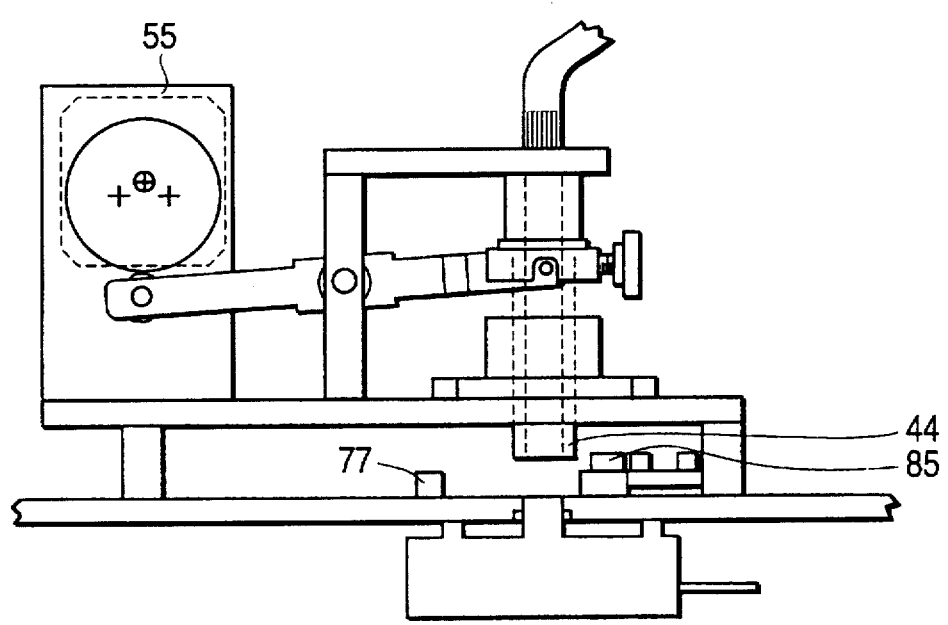
FIG. 7 is a side view in partial section of a third embodiment of the invention.
Figure 9:
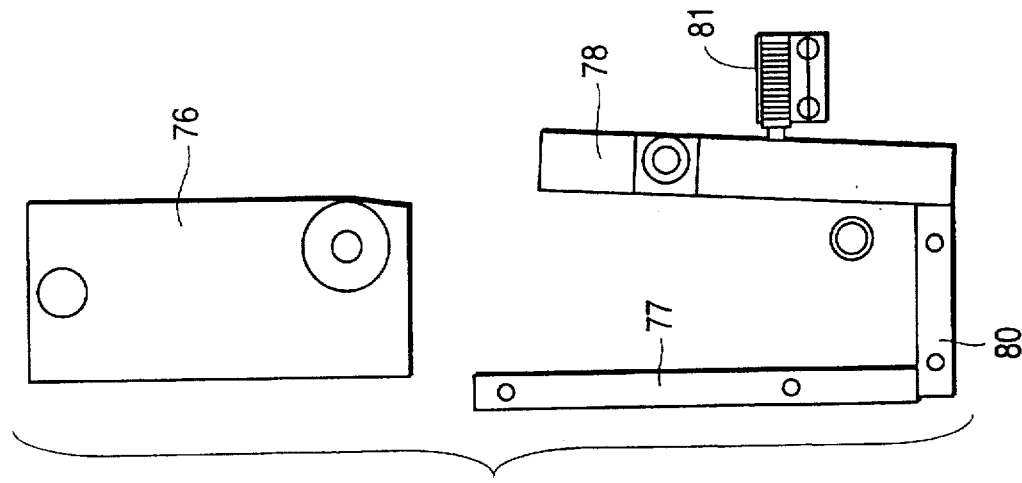
FIG. 9 is a partial top view of a loaded sample locator outside of the test position of the third embodiment of the invention.
Figure 8:
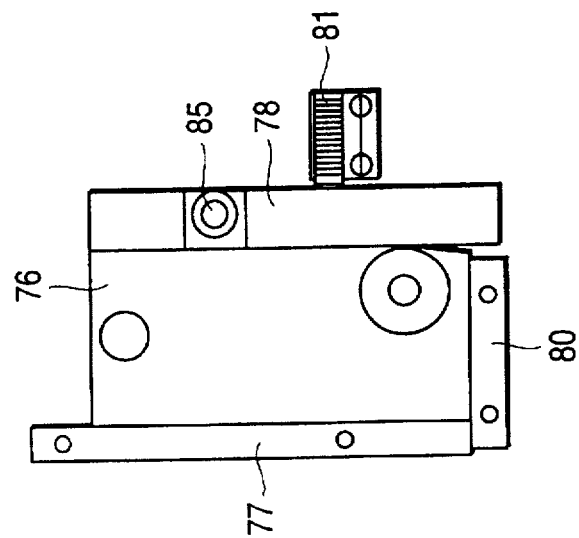
FIG. 8 is a top view of a loaded sample locator in the test position of the third embodiment of the invention.

A further embodiment of the invention is depicted in FIGS. 7–9. This embodiment employs an automatic, software-controlled probe elevator as described in the second embodiment which raises and lowers the probe onto the sample. The locator 76 used in this embodiment, as best seen in FIGS. 8 and 9, positions a single sample tablet under the probe. Locator 76 is manually inserted between side wall 77 and side wall 78 until it engages end wall 80. Sidewall 78 is biased in a first position (FIG. 9) by spring 81. As the locator 76 is inserted, force is exerted on a spring 81 and sidewall 78 pivots about fulcrum 85 to second position (FIG. 8) where it holds the locator in a position for the tablet to be measured. The locator of this embodiment holds a single tablet and is analogous to the locator depicted in FIG. 2 except the first well does not incorporate a slot feature. The masking element of the third embodiment incorporates the hood element 44 on the probe as described above in connection with the embodiment of FIGS. 3–6. When the locator is in place a command is provided which operates the motor 55 which in turn lowers the probe as described above in connection with the embodiment of FIGS. 3–6. When the probe is in the lowered position the measurement is performed.

In each of the embodiments, in connection with the measurement step, the grating of the spectrometer is rotated to vary the center frequency of the narrow band width light through the NIR spectrum and the instrument makes measurements at incrementally spaced wavelengths throughout the spectrum as the grating is rotated. The computer uses known techniques to analyze the resulting transmission measurements to analyze the sample including identifying the sample and quantifying the components of the sample.

In each of the embodiments the tablet is presented to the fiber optic bundle and the detector in a way to ensure that NIR radiation reaching the detector has passed through the sample and not leaked around it. Factors which contribute to minimizing the light leakage include the locator's sample well which is sized just large enough to allow a tablet to be inserted. In addition, the masking element which rests directly on the tablet which has an central aperture less than the size of the tablet also minimizes the possibility that NIR radiation will bypass the tablet. This feature could also be achieved by providing a fiber optic bundle with an end profile smaller than the top surface of the tablet. Lastly, the exit aperture is also formed smaller than the sample tablet.

In each of the embodiments described above the coupling distances between the probe, sample tablet and detector are kept to a minimum. The close coupling of the infrared radiation and the sample is an important feature of the invention because it minimizes the attenuation of the light energy. The actual distance between the fiber optics in the probe and the upper surface of the sample tablet will vary depending on the configuration and embodiment selected. In the embodiment depicted in FIG. 1 which employs a fixed probe, the distance between the probe and top surface of the tablet can range from 1/16 of an inch to as much as 5/32 of an inch. In connection with the embodiments which employ an automatic probe elevator as depicted in FIGS. 3 through 9, the distance between the probe and the top surface of the sample is between 0.010 and 0.020 inches.

Energy is also further conserved by directly transmitting the NIR light from the grating spectrometer through the fiber optic bundle which terminates within the probe where the radiation is directly transmitted through an air gap to the sample. In a preferred embodiment of the invention, predispersed NIR radiation is employed to minimize the heat to which the sample is subjected. In any spectroscopic analysis that subjects a sample to the full spectrum of wavelengths simultaneously, there is a risk that the attendant absorption of energy by the sample will cause it to heat and literally cook. The active compounds of some drug samples are particularly sensitive to thermal degradation. If the sample deteriorates, additional analysis of the sample cannot be performed to provide accurate results.

I claim:
1. A near infrared transmission spectrometer apparatus used for analyzing a tablet comprising,
    light source means for emitting light to a probe,
    said probe transmitting light to a tablet,
    detector means for receiving said transmitted light from said tablet,
    means positioned between said light source means and said detector means to receive a tablet locator, said tablet locator comprising a main body having an upper surface and a lower surface, said upper surface having an stepped well, said well having a first section and a second section centered on said first section, said second section having an exit portal smaller than said tablet, wherein said second section receives a tablet, said exit portal having a diameter less than the diameter of said tablet and providing a passage from said second section through said lower surface, and
    a masking element received in said first section, said masking element having a center opening which provides a passage for said light emitted from said probe to impinge upon said tablet in a beam with a boundary inside the boundary of the top surface of said tablet.

2. The near infrared transmission spectrometer apparatus as recited in claim 1 wherein said masking element comprises an annular ring having an outer diameter less than the diameter of said first section and a height less than the height of said first section, and having a central passage having a diameter substantially equal to said exit portal.

3. The near infrared transmission spectrometer apparatus as recited in claim 1 wherein said masking element comprises a hood attached to said light source means, said hood comprising an annular body element having a central aperture, said apparatus further comprising means to lower said hood into said well to enable said hood to contact said tablet.

4. The apparatus as recited in claim 3 further comprising means to automatically lower and raise said probe onto said tablet.

5. The apparatus as recited in claim 1 wherein said tablet locator comprises a plurality of said stepped wells.

6. The apparatus as recited in claim 5 wherein said tablet locator is arranged in arcuate configuration, the apparatus further comprising means to turn said arcuate configuration so that each said stepped well is moved into a position between said light source means and said detector means.

7. The apparatus recited in claim 6 further comprising motor means for turning a hub, and means for mounting said tablet locator to be rotated by said hub.

8. An apparatus as recited in claim 1, wherein said masking element is adapted to engage the top surface of a tablet in said second section of said well.

9. An instrument for making an NIR transmission measurement on a tablet comprising means to transmit a narrow band NIR light beam through said tablet, means to detect the NIR light amplitude transmitted through said tablet, and means to constrict the boundary of said light beam so that it is entirely within the boundary of a top surface of said tablet when it impinges upon said top surface.

10. A method of analyzing a tablet comprising presenting said tablet in an unwrapped state, passing an NIR light beam through said tablet in said unwrapped state, constricting the boundary of said light beam so that said light beam impinges upon the surface of said tablet with the boundary of said light beam entirely within the boundary of said surface of said tablet, and detecting the amplitude of the light from said light beam transmitted through said tablet.

* * * * *